United States Patent [19]

Zuckerwar et al.

[11] Patent Number: 5,140,992
[45] Date of Patent: Aug. 25, 1992

[54] PASSIVE FETAL MONITORING SENSOR

[75] Inventors: Allan J. Zuckerwar; Earl T. Hall, both of Newport News, Va.; Donald A. Baker, Spokane, Wash.; Timothy D. Bryant, Gloucester, Va.

[73] Assignee: The United States of America as represented by the Administrator of the National Aeronautics and Space Administration, Washington, D.C.

[21] Appl. No.: 552,670

[22] Filed: Jul. 16, 1990

[51] Int. Cl.⁵ ............................................. A61B 5/02
[52] U.S. Cl. ..................................... 128/715; 128/775
[58] Field of Search ............... 128/715, 698, 670, 773, 128/644, 662.04, 662.05, 662.06, 675, 681, 775, 687–690; 604/103; 73/721, 727, DIG. 4; 310/334, 338, 311–313 A, 357, 359

[56] References Cited

U.S. PATENT DOCUMENTS

| | | | |
|---|---|---|---|
| 4,122,843 | 10/1978 | Zdrojkowski | 128/644 |
| 4,191,193 | 3/1980 | Seo | 128/675 |
| 4,258,720 | 3/1981 | Flowers | 128/687 |
| 4,458,687 | 7/1984 | Dickson | 128/715 |
| 4,672,976 | 6/1987 | Kroll | 128/715 |
| 4,763,660 | 8/1988 | Kroll et al. | 128/644 |
| 4,781,200 | 11/1988 | Baker | 128/715 |
| 4,926,879 | 5/1990 | Sevrain et al. | 128/798 |
| 4,981,139 | 1/1991 | Pfohl | 128/715 |
| 5,049,130 | 9/1991 | Powell | 604/103 |

Primary Examiner—Kyle L. Howell
Assistant Examiner—J. R. Jastrzab
Attorney, Agent, or Firm—Kevin B. Osborne

[57] ABSTRACT

The invention is an ambulatory, passive sensor for use in a fetal monitoring system. The invention incorporates piezoelectric polymer film combined with a metallic mounting plate fastened to a belt and electrically connected to a signal processing unit by means of a shielded cable. The purpose of the sensor is to receive pressure pulses emitted from a fetus inside an expectant mother and to provide means for filtering out pressure pulses arising from other sources, such as the maternal heart.

16 Claims, 4 Drawing Sheets

PASSIVE FETAL MONITORING SENSOR

ORIGIN OF THE INVENTION

The invention described herein was jointly made by Government employees and an employee of a small entity contractor. In accordance with 35 USC 202, the contractor elected not to retain title.

BACKGROUND OF THE INVENTION

1. Field of the Invention

The present invention relates broadly to the field of biomedical transducers and more particularly to a passive sensor for fetal monitoring.

2. Related Art

Traditional methods of fetal monitoring include palpation and stethoscopic examination. These methods rely heavily on the treating physician's ability to receive sensing information and to subsequently process that information. Hence, such methods are inherently qualitative rather than quantitative.

Ultrasonic techniques improve upon traditional methods, but are intrusive and have possible deleterious effects on fetal development. Ultrasonic equipment is also costly, ill-suited to portability because of its size, and subject to error arising from imprecision in sensor alignment.

The prior art of fetal sensors includes acoustic sensors, which detect acoustic signals originating within the abdomen of the mother, interference sensors which detect and cancel interference from the mother's heartbeat, and accelerometers which detect fetal movement.

Prior interference sensors, such as those described in U.S. Pat. No. 4,784,154 (Shirley) have utilized a split polarization arrangement of the sensor assembly to cancel common mode signals arising from electromagnetic interference and radial stresses. Such an arrangement precludes the detection of fetal movement, because fetal movement generates common mode signals.

An overview of prior art monitors reveals two basic limitations: (1) they respond to fetal heart rate, thereby forfeiting the vast store of potential information contained in an instantaneous time history of pressure pulses; and (2) they are ill-suited to an ambulatory mode of operation, requiring operation in a clinical setting.

The monitor disclosed in U.S. Pat. No. 4,781,200 (Baker) surmounts these limitations. The described embodiments of Baker, however, reveal other difficulties. First, the high surface mass density and cantilevered arrangement of piezoelectric crystals used for signal detection make the crystals highly sensitive to movement by the mother. Consequently, the monitor of Baker, which consists of acoustic and interference sensors, together with a signal processing algorithm, must extract a relatively weak fetal signal from strong interference due to movement by the mother. Another limitation of Baker is the bulkiness of the cantilevered piezoelectric crystals which makes the belt on which they are mounted thick, cumbersome, unattractive, and generally impractical. Moreover, the monitor does not avail itself of array signal processing techniques, whereby several sensors operating in concert yield substantially more information than a sensor operating alone. Finally, in the mounting arrangement of Baker the sensors are not on a common plate, causing the sensors to yield different responses to a common mode signal.

Accordingly, it is an object of the invention to provide an ambulatory, passive sensor suitable for fetal monitoring.

It is a further object of the invention to provide a sensor suitable for use in a fetal heart monitoring system.

A further object of the invention is to provide an ambulatory, passive sensor exhibiting an acoustic impedance closely matching that of a human torso.

A further object of the invention is to receive pressure pulses emitted by the fetal heart and transform these pressure pulses into an electrical form suitable for processing by a signal processing means.

SUMMARY OF THE INVENTION

The present invention is an ambulatory, passive sensor for use in fetal monitoring. The term "ambulatory" denotes that the invention is suitable for wearing by the mother during her ordinary daily activities. The term "passive" denotes that the invention does not physically impinge upon the fetus, nor does it transmit energy flux into the fetus. The sensor receives pressure pulses emitted from the fetal heart and provides means for filtering out pressure pulses arising from other sources, such as the maternal heart.

DESCRIPTION OF THE PREFERRED EMBODIMENTS

Figure 1:
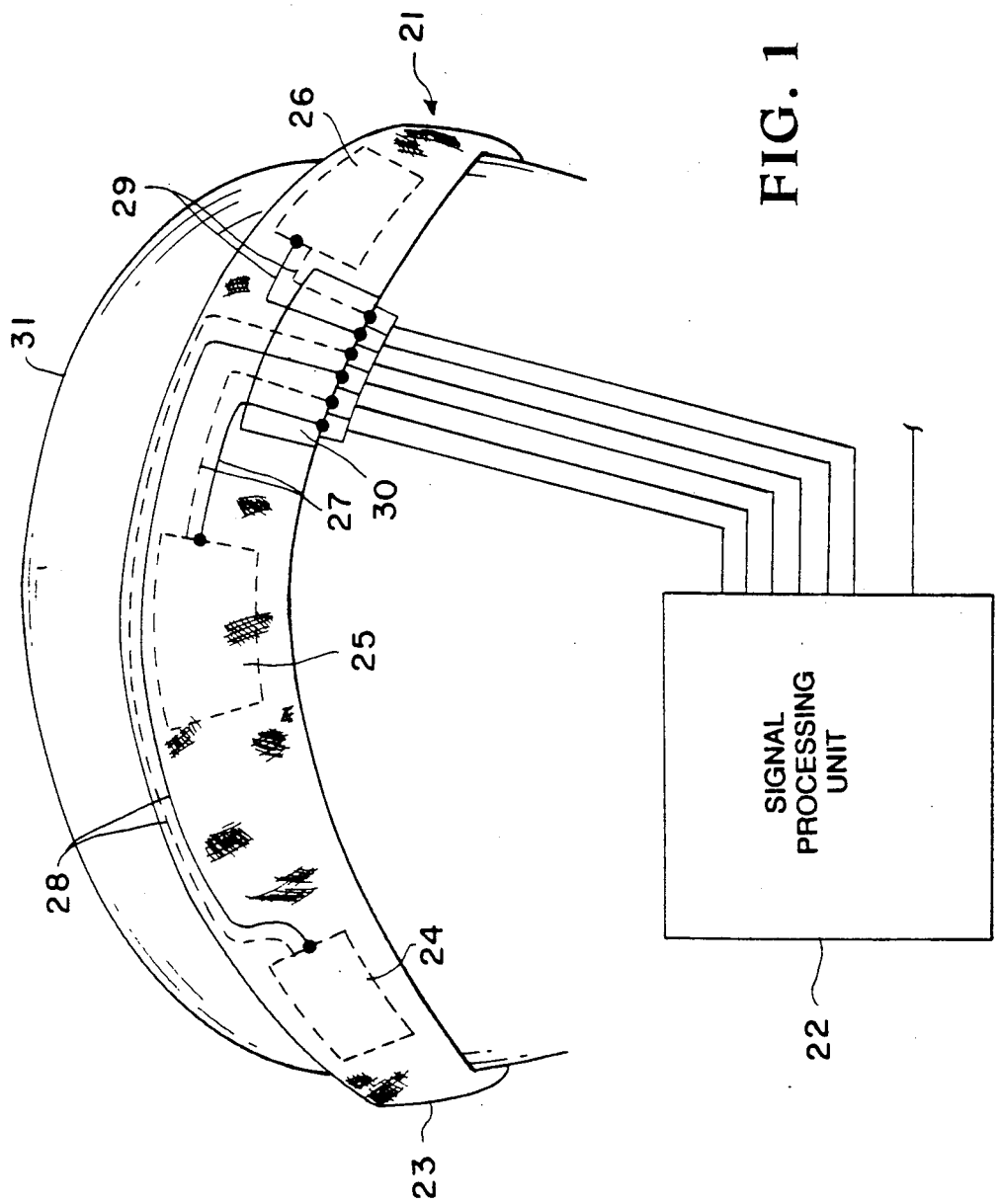
FIG. 1 illustrates a fetal monitoring system incorporating the ambulatory, passive fetal monitoring sensor of the present invention.

A preferred embodiment of the invention has a belt assembly 21 for connection to a signal processing unit 22, shown in FIG. 1. The belt assembly 21 has a belt 23, one or more sensor stations 24, 25, and 26, pairs of cables 27, 28 and 29, and a cable connector 30. The belt 23 is worn snugly but comfortably around the mother's abdomen 31. An especially preferred embodiment features three sensor stations. The belt 23 is made of any familiar material exhibiting strength and resistance to stretching, such as woven nylon or canvas, with typical dimensions of 30" long × 1-¼" wide × ⅛" thick. The inelasticity of the belt 23 ensures internal pressure pulses will compress the piezoelectric sensing means and suppress any acceleration of the sensing means resulting from internal pressure pulses.

Figure 2:
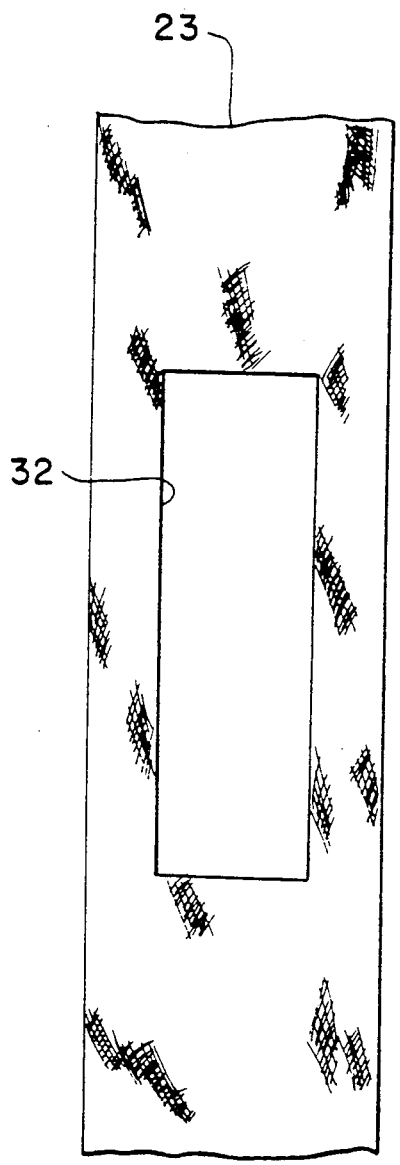
FIG. 2 is a top view of a belt illustrating the location of a typical cutout.

As shown in FIG. 2, the belt 23 provides a cutout 32 for each sensor station. Each cutout is typically 1-¾" × ⅜". In the especially preferred embodiment the three sensor stations are located at the center of the belt and 4-½" to either side of the center. In the especially preferred embodiment, the belt is fastened by a commercially available fastening material like "VELCRO"

brand hook and loop fasteners, but may be fastened by any appropriate means.

Figure 3:
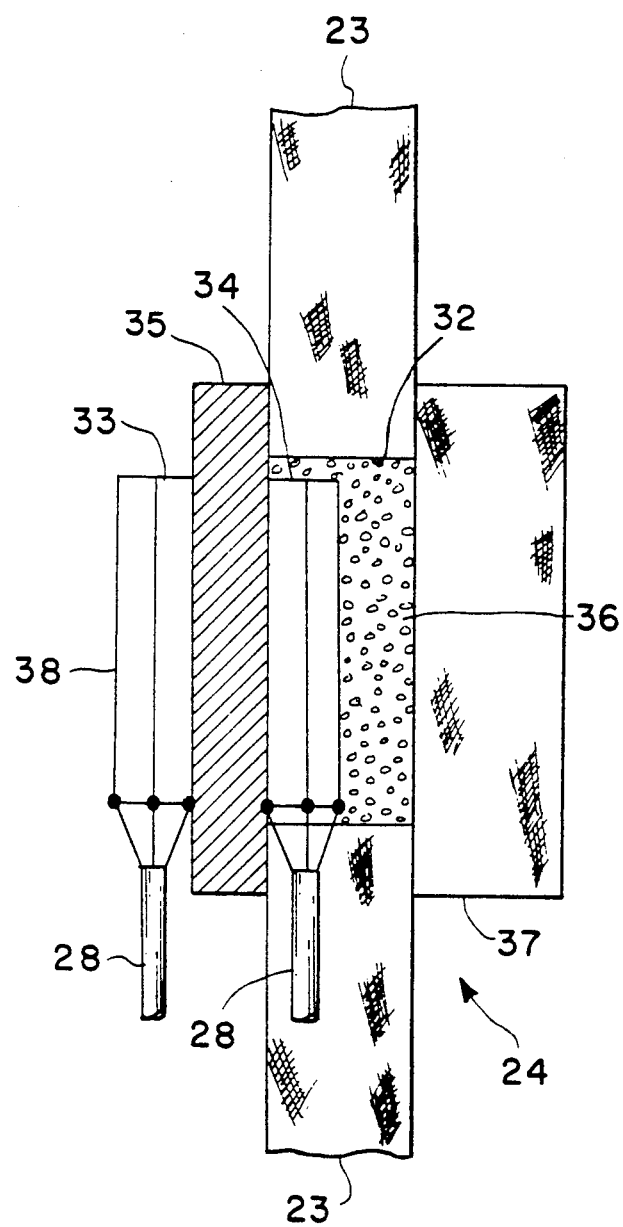
FIG. 3 is a cross-sectional view of a pair of sensor assemblies.

The components of a sensor station 24, shown in FIG. 3, are an inner sensor assembly 33, and outer sensor assembly 34, a mounting plate 35, acoustic insulation 36, a flap 37. The inner and outer sensor assemblies, which are identical in construction, provide the signals subsequently processed in the signal processing unit 22.

Figure 4:
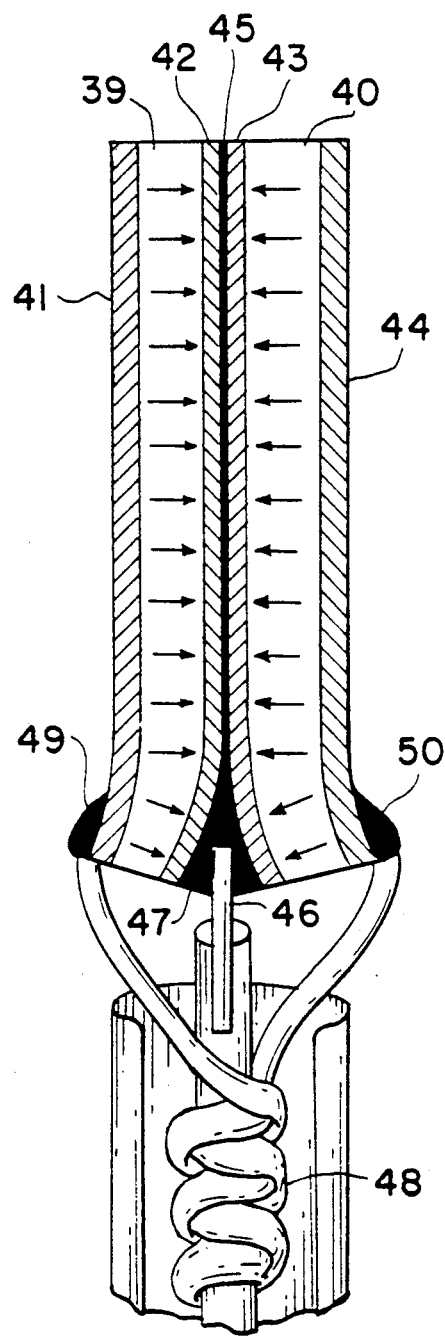
FIG. 4 is a cross-sectional view illustrating a method of constructing a sensor assembly.

FIG. 4 illustrates the construction of sensor assemblies 33,34. Each sensor assembly 33,34 contains two strips 39 and 40 of piezoelectric polymer film, such as polyvinylidene fluoride ($PVF_2$), each typically 1" long × ½" wide × 0.004" thick. The two strips of film are coated on both sides with thin metallic layers, 41,42,43 and 44, which serve as electrodes, and are bonded together by means of a thin layer of epoxy 45. The center electrodes 42,43 are bonded to the center conductor 46 of a coaxial cable, and the outer electrodes 41,44 are together bonded to the cable shield 48, which serves as the outer conductor. The bonds between the film electrodes 41,42,43,44 and cable conductors 46,48 are beads 47,49,50 of conducting epoxy.

The polymer film derives its piezoelectric property from the fact that it is electrically prepolarized; that is, it has a permanent electric dipole moment. The orientation of the dipoles, indicated by the arrows in FIG. 4, is such that the layers 42,43 contacting the positive (or negative) charge are joined together, and the layers 41,44 contacting the negative (or positive) charge are joined together. A time-varying pressure incident upon either electrode 41,44 changes the net polarization and produces a proportional voltage across the points connected to cable conductors 46,48.

In the arrangement shown in FIG. 4 the center conductors 42,43,46 are completely shielded by the outer conductors 41,44,48, along the entire signal path from a sensor assembly 33 or 34 to the signal processing unit 22. This shielding is only partially effective in rejecting undesirable background signals, such as radio-frequency interference and 60 Hz pickup from electrical lines, and for this reason a shielding electrode 60 (not shown in FIG. 4); has been implemented, as described below in reference to FIG. 6. In each sensor assembly the two metallized polymer films 39,40 behave as a single unit, mechanically in series and electrically in parallel.

As shown in FIG. 3, sensor assemblies 33,34 are inserted into a respective cutout 32 located at each sensor station 24,25, and 26 shown in FIG. 1. An outer electrode 41 or 44 from each assembly is bonded with epoxy to a mounting plate 35 which is fastened to the belt 23 by sewing, riveting, or any means that will ensure rigid attachment. Typical dimensions for the mounting plate are 1-½" long × 1" wide × 0.010–0.015" thick.

The mounting plate 35 fulfills two important functions. First, its large flexural rigidity precludes flexural deformation of the sensors, as may be caused by motion of the mother. Secondly, acoustical signals originating from within the mother's body are incident upon surface 38 and are received by both the inner sensor assembly 33 and the outer sensor assembly 34. Acceleration of the mounting plate 35, on the other hand, as may be caused by rigid-body motion of the mother or by fetal movement, produces like signals in both sensor assemblies 33 and 34. Thus the detected signal contains components due to both acoustical sources and rigid-body motion, but acceleration compensated signal contains the acoustic component alone because the rigid-body component is cancelled. Consequently, operation in the acceleration compensated mode permits one to separate acoustic sources from rigid-body motion. Further, to prevent acoustical signals generated external to the mother, e.g., ambient noise, from reaching the external sensor assembly 34, the adjacent region of the cutout 32 is packed with an acoustical insulating material 36, such as wool made from Kevlar. A flap 37 holds the acoustic insulating material in place.

The pair of coaxial cables 27,28, or 29 conducts the signals from the sensor stations 24,25, or 26 through connector 30 to the signal processing unit 22, shown in FIG. 1. In an ambulatory monitor the signal processing unit 22 is a small battery-operated package mounted on the belt 23. It may be any device which performs the following functions: (1) acquiring acoustic signals originating from within the mother's abdomen; (2) detecting and cancelling interference contributions (e.g., mother's heartbeat and ambient noise) in order to isolate the pressure pulses emitted by the fetal heart; (3) detecting fetal movement; and (4) analyzing fetal heart signals to determine the state of fetal wellness according to some established criterion.

Experience has revealed that the quality of the signal is sensitive to fetal position and thus the location of a sensor on the mother's body. The use of multiple sensors, numbering three in the embodiment described here as an example, permits the observer to select the signal of best quality for subsequent signal processing.

In an alternate embodiment of the invention, each sensor 33,34 is fabricated from a single strip of piezoelectric polymer film. By removing film 40, the metallic layer 42 of the remaining film is electrically connected to mounting plate 35 and metallic layer 41 is electrically insulated from mounting plate 35. Hence, mounting plate 35 functions as an electrical shield.

Figure 5:
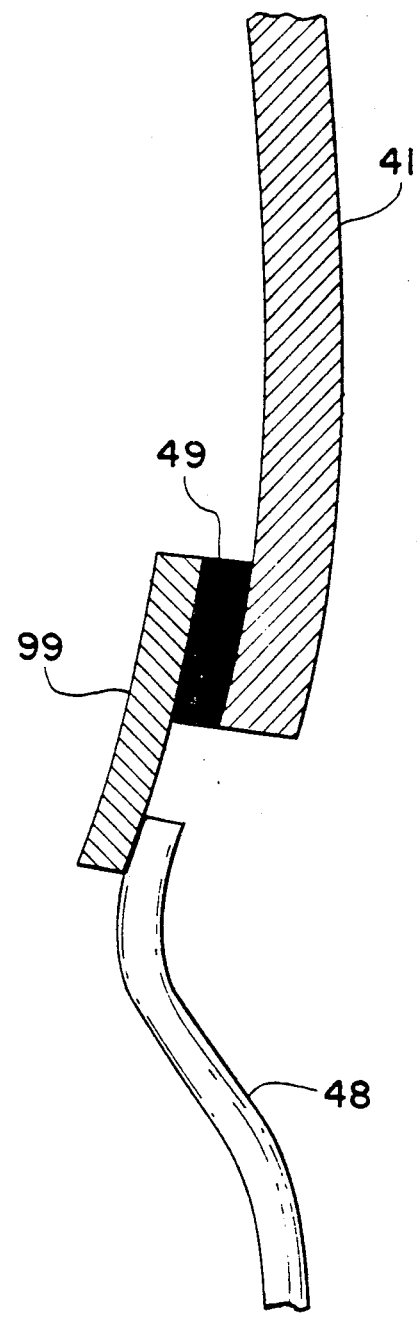
FIG. 5 illustrates a metallic tab used to bond an electrode with conducting epoxy.

In another embodiment of the invention, a metallic tab 99, shown in FIG. 5 is bonded to electrode 41 with conducting epoxy at the location indicated by 49. The tab 99 contains a leaf which is spot-welded to coaxial cable shield 48. Another tab 99 is bonded to electrode 44 at location 50 and spot-welded to shield 48. This arrangement makes the connections considerably more compact and sturdy.

Figure 6:
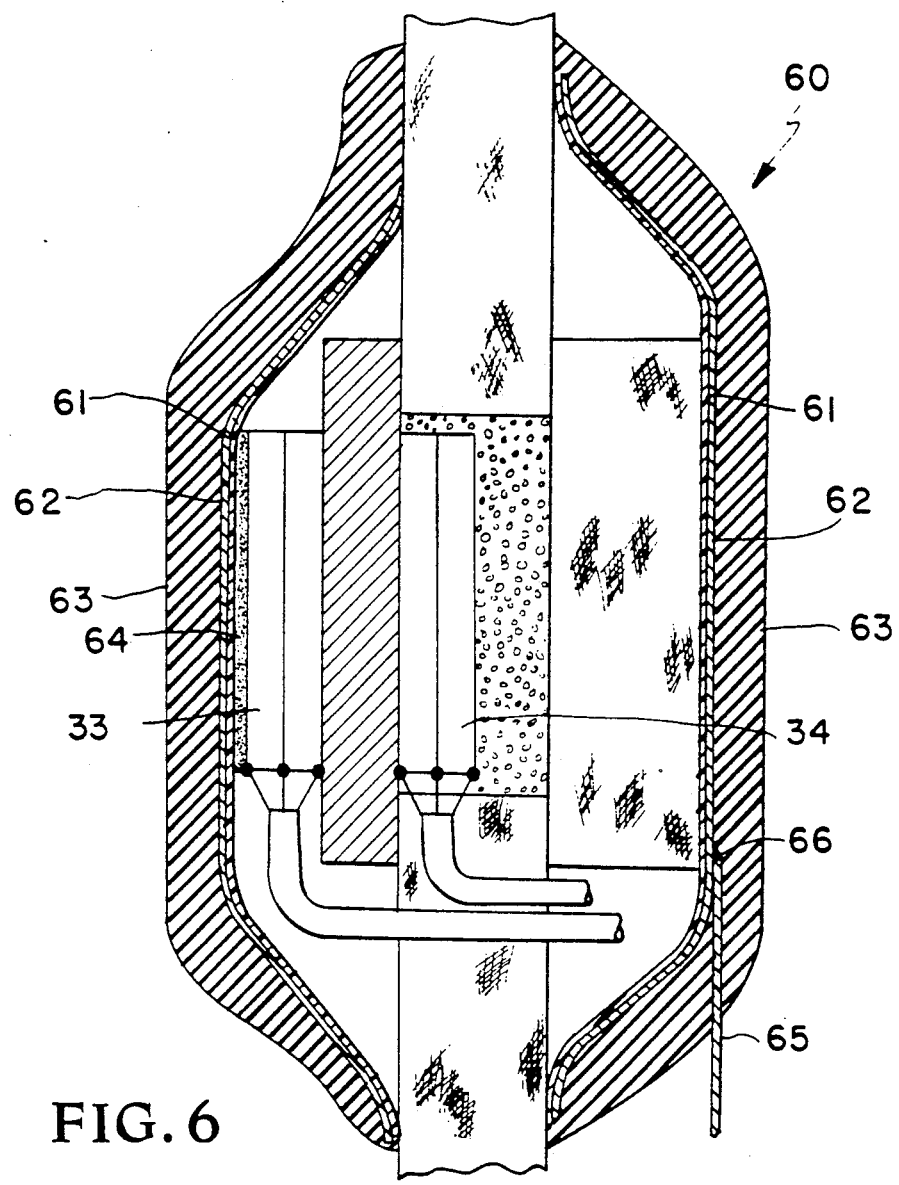
FIG. 6 illustrates a fetal monitoring system incorporating a shielding electrode according to the present invention.
Figure 7:
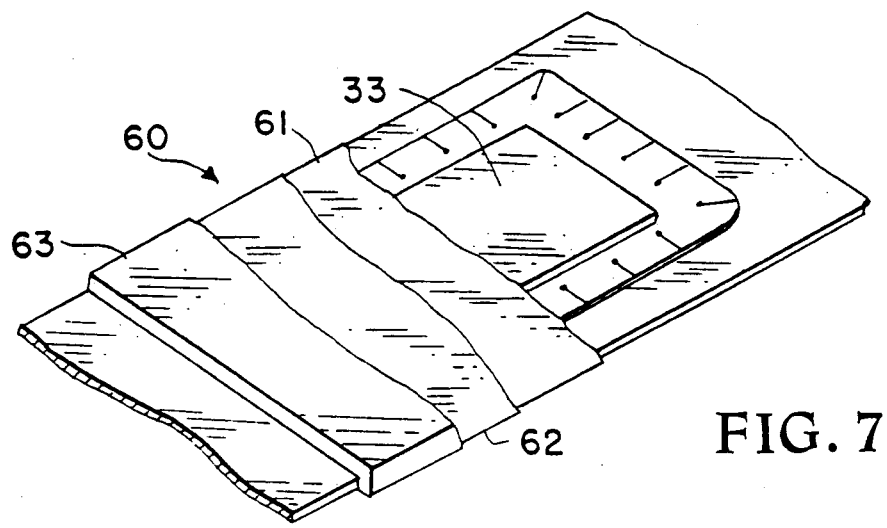
FIG. 7 is a cutaway view of the shielding electrode of FIG. 6.

Another embodiment of the invention uses a shielding electrode 60, shown in FIGS. 6 and 7, which is effective in eliminating 60 Hz interference, and is especially useful in clinical studies, where monitoring instrumentation may be connected to a 60 Hz electrical power source. The high electrical resistivity of the piezoelectric polymer film makes it particularly susceptible to 60 Hz interference. FIG. 6 shows a cross-sectional view, and FIG. 7 a cutaway view, of the shielding electrode attached to a sensor assembly. In the example selected for illustration, the shielding electrode 60 consists of a layer of copper 62 deposited on a "KAPTON" brand polyimide, foil 61, which is bonded to the internal sensor assembly 33 by means of a contact adhesive 64, such as "SUPER 77" brand adhesive, manufactured by the 3M Company. The layer of copper 62 and the layer of foil 61 can be of virtually any thickness which will permit the layers to effectively be wrapped around the sensor assemblies 33 and 34. A thickness of 0.0014" of copper layer 62 and 0.0016" of "KAPTON" brand polyimide layer 61 has been found beneficial. The shielding electrode 60 completely encircles the sensor assemblies 33 and 34. A wire 65 is soldered to the copper layer 62 at a location 66 on the external side of the sensor station. When the wire 65 is connected to earth ground, the 60 Hz interference virtually disappears. A layer of RTV silicone rubber 63, typically 1/32" to 1/16" thick, provides electrical isolation of the patient without compromising acoustic transmission into the sensor assemblies 33 and 34.

What is claimed is:

1. An ambulatory passive fetal monitoring sensor comprising:
   a substantially inelastic garment for wear by an expectant mother about the mother's torso;
   one or more sensor stations mounted on said inelastic garment, each of said sensor stations comprising:
   a. a rigid metallic mounting plate having first and second substantially parallel surfaces;
   b. a first piezoelectric polymer film sensing means for sensing internal pulses from the mother including a heartbeat of a fetus, a first surface of which is affixed to the first surface of said mounting plate and a second surface of which is adopted to be positioned flush upon the mother's torso; and
   c. a second piezoelectric polymer film sensing means for sensing rigid body motion of the mother, said second piezoelectric polymer film sensing means affixed to the second surface of said mounting plate.

2. The invention as defined in claim 1 wherein each of said one or more sensor stations is mounted in a cutout in said inelastic garment.

3. The invention as defined in claim 1, wherein there are three or more sensor stations.

4. The invention as defined in claim 1, further comprising acoustic insulating means packed between said second piezoelectric polymer film sensing means and said elastic garment to isolate said second piezoelectric polymer film sensing means from ambient noise.

5. The invention as defined in claim 4, wherein each of said one or more sensor stations is mounted in a cutout in said elastic garment such that said second piezoelectric polymer film sensing means is positioned within the cutout and said acoustic insulating means is packed in the cutout.

6. The invention as defined in claim 1, further comprising cable means for electrically connecting an output of each sensor station to a signal processing means.

7. The invention as defined in claim 1, wherein said inelastic garment has an inelasticity which ensures contact with the mother's torso to permit compression of said first piezoelectric polymer film sensing means by internal pulses of the mother and to suppress any acceleration of the sensor stations caused by the internal pulses.

8. An ambulatory passive fetal monitoring sensor comprising:
   a substantially inelastic garment for wear by an expectant mother about the mother's torso;
   one or more sensor stations mounted on said inelastic garment, each of said sensor stations comprising:
   a. a rigid, metallic mounting plate having first and second substantially parallel surfaces;
   b. a first piezoelectric polymer film sensing means for sensing internal pulses from the mother including a heartbeat of a fetus, a first surface of which is affixed to the first surface of said mounting plate and a second surface of which is adopted to be positioned flush upon the mother's torso; and
   c. a second piezoelectric polymer film sensing means for sensing rigid body motion of the mother, said second piezoelectric polymer film sensing means affixed to the second surface of said mounting plate; and
   a shielding electrode surrounding each of said sensor stations, said shielding electrode comprising an insulating film bonded to a metallic film, which is coated with an insulating layer separating the shielding electrode from the mother's torso, whereby the mother is electrically insulated from sensor station and acoustic transmission from the mother and fetus to said first piezoelectric polymer film sensing means is not compromised.

9. The invention as defined in claim 8 wherein said insulating film is a polyimide foil.

10. The invention as defined in claim 8 wherein said metallic film is copper.

11. The invention as defined in claim 8 wherein said insulating layer separating the electrode from the mother's torso is a silicone rubber.

12. The invention as defined in claim 8, wherein each of said one or more sensor stations is mounted in a cutout in said inelastic garment.

13. The invention as defined in claim 8, wherein there are three or more sensor stations.

14. The invention as defined in claim 8, further comprising acoustic insulating means packed between said second piezoelectric polymer film sensing means and said elastic garment to isolate said second piezoelectric polymer film sensing means from ambient noise.

15. The invention as defined in claim 14, wherein each of said one or more sensor stations is mounted in a cutout in said elastic garment such that said second piezoelectric polymer film sensing means is positioned within the cutout and said acoustic insulating means is packed in the cutout.

16. The invention as defined in claim 8, wherein said inelastic garment has an inelasticity which ensures contact with the mother's torso to permit compression of said first piezoelectric polymer film sensing means by internal pulses of the mother and to suppress any acceleration of the sensor stations caused by the internal pulses.

* * * * *